(12) United States Patent
Soykan et al.

(10) Patent No.: US 8,641,659 B2
(45) Date of Patent: Feb. 4, 2014

(54) METHOD AND DEVICE TO TREAT KIDNEY DISEASE

(75) Inventors: Orhan Soykan, Shoreview, MN (US); Carl Schu, Plymouth, MN (US); Kimberly Chaffin, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

(21) Appl. No.: 13/399,910

(22) Filed: Feb. 17, 2012

(65) Prior Publication Data
US 2012/0220926 A1    Aug. 30, 2012

Related U.S. Application Data

(60) Provisional application No. 61/444,092, filed on Feb. 17, 2011.

(51) Int. Cl.
*A61M 1/00* (2006.01)
(52) U.S. Cl.
USPC .............................................. 604/29; 604/27
(58) Field of Classification Search
USPC .................................................... 604/27–29
See application file for complete search history.

(56) References Cited

U.S. PATENT DOCUMENTS

| | | | |
|---|---|---|---|
| 3,370,710 A | 2/1968 | Bluemle, Jr. | |
| 3,669,878 A | 6/1972 | Marantz | |
| 3,669,880 A | 6/1972 | Marantz | |
| 3,809,241 A | 5/1974 | Alvine | |
| 3,810,259 A * | 5/1974 | Summers | 600/30 |
| 3,850,835 A | 11/1974 | Marantz | |
| 3,989,622 A | 11/1976 | Marantz | |
| 4,278,092 A * | 7/1981 | Borsanyi et al. | 604/175 |
| 4,460,555 A | 7/1984 | Thompson | |
| 4,581,141 A | 4/1986 | Ash | |
| 4,650,587 A | 3/1987 | Polak | |
| 4,826,663 A | 5/1989 | Alberti | |
| 6,627,164 B1 | 9/2003 | Wong | |
| 6,818,196 B2 | 11/2004 | Wong | |

(Continued)

FOREIGN PATENT DOCUMENTS

| | | |
|---|---|---|
| EP | 0022370 A1 | 1/1981 |
| WO | 2005023589 A2 | 3/2006 |
| WO | 2009157677 A1 | 12/2009 |
| WO | 2010052705 A1 | 6/2010 |

OTHER PUBLICATIONS

Roberts M, The regenerative dialysis (REDY) sorbent system, Nephrology, 1998, 275-278: 4.

(Continued)

*Primary Examiner* — Manuel Mendez
*Assistant Examiner* — Rebecca E Eisenberg
(74) *Attorney, Agent, or Firm* — Hahn & Voight PLLC; Roger C. Hahn

(57) ABSTRACT

The invention relates to a method and device for dialysis and or bulk fluid removal by generating a fibrosis chamber within a body cavity and performing dialysis or bulk fluid removal. An implantable medical device is described having a fibrosis chamber and a pump. A dialysis chamber and an optional electrodialysis unit can further be provided. An additional controller uses sensory feedback to regulate the fluid levels by altering the extracellular fluid retention within the fibrosis chamber. This device can be used for the treatment of patients with chronic kidney disease who may also be suffering from cardiorenal syndrome and hypertension.

14 Claims, 11 Drawing Sheets

(56) References Cited

U.S. PATENT DOCUMENTS

| | | | |
|---|---|---|---|
| 6,878,283 B2 | 4/2005 | Thompson | |
| 7,023,359 B2 | 4/2006 | Goetz | |
| 7,566,432 B2 | 7/2009 | Wong | |
| 7,736,507 B2 | 6/2010 | Wong | |
| 7,776,210 B2 | 8/2010 | Rosenbaum | |
| 8,267,885 B2 * | 9/2012 | Landherr et al. | 604/29 |
| 2002/0112609 A1 | 8/2002 | Wong | |
| 2004/0049288 A1 * | 3/2004 | Levin | 623/23.65 |
| 2004/0143173 A1 | 7/2004 | Reghabi et al. | |
| 2004/0147871 A1 * | 7/2004 | Burnett | 604/9 |
| 2005/0096582 A1 * | 5/2005 | Burnett | 604/9 |
| 2006/0058731 A1 * | 3/2006 | Burnett et al. | 604/29 |
| 2006/0076295 A1 | 4/2006 | Leonard | |
| 2008/0006570 A1 | 1/2008 | Gura et al. | |
| 2008/0183126 A1 * | 7/2008 | Landherr et al. | 604/29 |
| 2009/0127193 A1 | 5/2009 | Updyke et al. | |
| 2009/0131858 A1 | 5/2009 | Fissell | |
| 2009/0282980 A1 | 11/2009 | Gura | |
| 2010/0022936 A1 | 1/2010 | Gura | |
| 2010/0078381 A1 | 4/2010 | Merchant | |
| 2010/0078387 A1 | 4/2010 | Wong | |
| 2010/0084330 A1 | 4/2010 | Wong | |
| 2010/0326911 A1 | 12/2010 | Rosenbaum | |
| 2011/0017665 A1 | 1/2011 | Updyke | |
| 2011/0208319 A1 * | 8/2011 | Laster | 623/23.65 |

OTHER PUBLICATIONS

Marchant, et. al., In vivo Biocompatibility Studies I: The Cage Implant System and a Biodegradable Hydrogel, J. Biomed. Mat, Res., 1983, 301-325 : 17.

Siegenthalar, et. al., Pulmonary fluid status monitoring with intrathoracic impedance, Journal of Clinical Monitoring and Computing, 2010, 449-451 : 24.

Wang, Fundamentals of intrathoracic impedance monitoring in heart failure, Am. J. Cardiology, 2007, 3G-10G : Suppl.

Bleyer, et. al., Sudden and cardiac death rated in hemodialysis patients, Kidney International, 1999, 1553-1559 : 55.

PCT/US2012/025711 International Search Report mailed Jul. 4, 2012.

* cited by examiner

METHOD AND DEVICE TO TREAT KIDNEY DISEASE

CROSS-REFERENCE TO RELATED APPLICATIONS

This application claims benefit of priority to U.S. Provisional Patent Application Ser. No. 61/444,092, filed Feb. 17, 2011, which is incorporated herein by reference.

FIELD OF THE INVENTION

The invention relates to a partially or fully implantable medical device for dialysis or fluid removal from the peritoneum that overcomes problems with fibrogenesis and infection. The medical device has a partially porous mesh that forms a fibrosis cage upon implantation into a patient, an optional dialysis chamber inside the partially porous mesh or extracorporeally having an inlet and an outlet, and a pumping means for pumping fluid out of the fibrosis cage. The systems and methods of the invention optionally include an implantable dialyzer and or electrodialyzer. The invention further relates to methods of introducing a dialysate directly into a patient and dialyzing blood intracorporeally or extracorporeally.

BACKGROUND

Kidneys of the human body function to remove excess fluids as well as some ions. The functional unit of the kidney is the nephron. A nephron consists of a filtering unit of tiny blood vessels called a glomerulus attached to a tubule. When blood enters the glomerulus, it is filtered and the remaining fluid then passes along the tubule. In the tubule, chemicals and water are either added to or removed from this filtered fluid according to the body's needs, and the final product is urine, which is excreted.

In patients with chronic kidney disease, kidney function is severely compromised. Chronic kidney disease (CKD), also known as chronic renal disease, is a progressive loss in renal function over a period of months or years. The most severe stage of CKD is End Stage Renal Disease (ESRD), which occurs when the kidneys cease to function. The two main causes of CKD are diabetes and high blood pressure, which are responsible for up to two-thirds of the cases. Heart disease is the leading cause of death for all people having CKD. Excessive fluid can accumulate in patients suffering from ESRD. The mortality rate of ESRD patients who receive traditional hemodialysis therapy is 24% per year with an even higher mortality rate among diabetic patients. Fluid accumulates in ESRD patients because the kidneys can no longer effectively remove water and other fluids from the body. The fluid accumulates first in the blood and then accumulates throughout the body, resulting in swelling of the extremities and other tissues as edema. This accumulation of fluid causes increased stress on the heart, in turn causing significant increases in blood pressure or hypertension, which can lead to heart failure.

Although the population of patients afflicted with CKD grows each year, there is no cure. Current treatments for CKD seek to slow the progression of the disease. However, as the disease progresses, renal function decreases, and, eventually, renal replacement therapy is employed to compensate for lost kidney function. Renal replacement therapy entails either transplantation of a new kidney or dialysis.

Methods to treat kidney disease require the processing of blood to extract waste components such as urea and ions. The traditional treatment for kidney disease involves dialysis. Dialysis emulates kidney function by removing waste components and excess fluid from a patient's blood. This is accomplished by allowing the body fluids, usually the blood, to come into the close proximity with the dialysate, which is a fluid that serves to cleanse the blood and actively remove the waste components and excess water. During this process, the blood and dialysate are separated by a dialysis membrane, which is permeable to water, small molecules (such as urea), and ions but not permeable to the cells. Each dialysis session lasts a few hours and may be repeated as often as three times a week.

Traditional processes, such as dialysis, require extracorporeal processing of body fluids. Once the blood is purified, it is then returned to the patient. Although effective at removing waste components from blood, dialysis treatments are administered intermittently and, therefore, do not emulate the continuous function of a natural kidney. Once the dialysis session is completed, the fluid begins to accumulate again in the tissues of the patient. The benefits of dialysis notwithstanding, statistics indicate that three out of five dialysis patients die within five years of commencing treatment. Studies have shown that increasing the frequency and duration of dialysis sessions can improve the survivability of dialysis patients. Increasing the frequency and duration of dialysis sessions more closely resembles the continuous kidney function sought to be emulated. However, the extracorporeal processing of the body fluids increases the discomfort, inconvenience and the costs associated with treatment. There is also an additional risk of infection, which mandates that the procedures be carried out under the supervision of trained medical personnel.

Wearable dialysis units have been conceived in which the various components of the dialysis unit are miniaturized and made portable. The utility of these units remains limited due to the requirement that the blood must be brought outside of the body for filtering and due to the necessity for frequent servicing of the parts.

An alternative to a wearable dialysis system is an implantable dialysis device. With conventional implantable dialysis devices, most of the components are implanted, and the blood does not leave the patient's body. This type of unit suffers from difficulties related to the need for surgery to replace the internal parts, generally resulting from growth of tissue over the surfaces of the device that are exposed to tissue fluids, which results in reduced efficiency of the filtration.

Another clinical solution for kidney disease is peritoneal dialysis. In peritoneal dialysis, dialysate is infused into the peritoneal cavity. The peritoneal membrane serves as a natural dialyzer, and waste components diffuse from the patient's bloodstream across the peritoneal membrane into the dialysis solution via an osmotic gradient. Under local anesthesia, a many-eyed catheter is sutured in place in the peritoneum and a sterile dressing is applied. The amount and the kind of dialysate and the length of time for each exchange cycle vary with the age, size, and condition of the patient. There are three phases in each cycle. During inflow, the dialysate is introduced into the peritoneal cavity. During equilibration (swell), the dialysate remains in the peritoneal cavity. By means of osmosis, diffusion, and filtration, the needed electrolytes pass via the vascular peritoneum to the blood vessels of the abdominal cavity, and the waste products pass from the blood vessels through the vascular peritoneum into the dialysate. During the third phase (drain), the dialysate is allowed to drain from the peritoneal cavity by gravity. The dialysis solution is removed, discarded, and replaced with fresh dialysis solution on a semi-continuous or continuous basis. Patients are able to replace the fluid periodically and care for the access ports. This particular treatment causes discomfort due to excess amounts of fluid being pumped in and out of the abdominal area and retrograde flow into the bloodstream, which can increase fluid retention and the risk of infections. Further, medication for pain may be necessary.

Peritoneal dialysis may result in several complications, including perforation of the bowel, peritonitis, atelectasis, pneumonia, pulmonary edema, hyperglycemia, hypovolemia, hypervolemia, and adhesions. Peritonitis, the most common problem, is usually caused by failure to use aseptic technique and is characterized by fever, cloudy dialysate, leukocytosis, and abdominal discomfort. There is a need for a dialysis system for peritoneal dialysis and/or fluid removal that is safe and effective and that markedly improves a patient's comfort and quality of life over conventional systems and methods. It would be advantageous for the system to be safe enough for continuous use and allow the patient to carry out normal daily activities. Hence, there is an unmet medical need to build a wearable or implantable medical device to treat chronic kidney disease that can provide more frequent or continuous treatment with less discomfort and a lower risk of infection.

SUMMARY OF THE INVENTION

The invention is directed to a medical device for dialysis within the peritoneum that can be partially or fully implanted. Related medical systems and methods for intra-corporeal dialysis are provided.

In one embodiment, a partially implantable medical device has a partially porous mesh that forms a fibrosis cage upon implantation into a patient, and a pumping means for pumping fluid into and out of the fibrosis cage. In any embodiment, the pumping means can be positioned inside the partially porous mesh, outside the mesh or adjacent to the mesh.

In another embodiment, the medical device has a dialysis chamber having an inlet and an outlet inside of a partially porous mesh.

In another embodiment, the medical device has a pumping means positioned inside the partially porous mesh, outside the mesh or adjacent to the porous mesh.

In another embodiment, the medical device has a partially porous mesh that forms a fibrosis cage upon implantation into a patient, an electrodialyzer in fluid communication with a dialysis chamber inside the partially porous mesh, and a pumping means for pumping fluid into and out of the fibrosis cage.

In another embodiment, the medical device has a partially porous mesh that forms a fibrosis cage upon implantation into a patient, an electrodialyzer in fluid communication with a dialysis chamber, and a pumping means for pumping fluid into and out of the fibrosis cage.

In another embodiment, the medical device has a partially porous mesh that forms a fibrosis cage upon implantation into a patient, an electrodialyzer in fluid communication with a dialysis chamber, and a pumping means for pumping fluid into and out of the fibrosis cage, wherein the pumping means is located outside of the fibrosis cage.

In another embodiment, the medical device has a partially porous mesh that forms a fibrosis cage upon implantation into a patient, a pump that is placed inside or outside of the partially porous mesh to provide the pumping means for pumping the fluid out of the fibrosis cage, and a catheter to bring the fluid out of the body or a catheter to bring the fluid into the bladder.

In another embodiment, the medical device has a pumping means located inside of the fibrosis cage.

In another embodiment, the medical device has a partially porous mesh that forms a fibrosis cage upon implantation into a patient, an electrodialyzer in fluid communication with a dialysis chamber and the electrodialyzer outside the partially porous mesh, and a pumping means for pumping fluid into and out of the fibrosis cage.

In another embodiment, the medical device has a partially porous mesh that forms a fibrosis cage upon implantation into a patient, an electrodialyzer in fluid communication with a dialysis chamber and the electrodialyzer outside the partially porous mesh and the body of a patient, and a pumping means for pumping fluid into and out of the fibrosis cage.

In another embodiment, the medical device has a means for sensing a fluid volume of the patient, wherein the means for sensing fluid volume is an electrical impedance plethysmography or an arterial pressure measurement.

In another embodiment, the medical device has a means to deliver fresh dialysate to the dialysis chamber.

In another embodiment, the medical device has a controller for regulating the fluid volume of the patent and adjusting a clearance rate of the patient.

In yet another embodiment, the medical device has a partially porous mesh that forms a fibrosis cage upon implantation into a patient, an electrodialyzer inside the partially porous mesh, and a pumping means for pumping fluid into and out of the fibrosis cage.

In a medical system of the invention, one embodiment has a partially porous mesh that forms a fibrosis cage upon implantation into a patient, a dialysis chamber inside the partially porous mesh having an inlet and an outlet, a pumping means for pumping fluid into and out of the fibrosis cage, a optional means for sensing a fluid volume of the patient, an external dialysate cleanser, and a controller such as a pump controller known to those of skill in the art for regulating the fluid volume and adjusting a clearance rate of the patient.

In another medical system of the invention, one embodiment has a partially porous mesh that forms a fibrosis cage upon implantation into a patient, an electrodialyzer in fluid communication with a dialysis chamber inside the partially porous mesh, a pumping means for pumping fluid into and out of the fibrosis cage, a optional means for sensing a fluid volume of the patient, and a controller for regulating the fluid volume and adjusting a clearance rate of waste components in the patient.

In another embodiment, the medical device has a partially porous mesh that forms a fibrosis cage upon implantation into a patient, an electrodialyzer inside the partially porous mesh, and a pumping means for pumping fluid into and out of the fibrosis cage.

In another embodiment, the medical device has a pumping means that is a bellows pump.

In another embodiment, the medical device has a pressure sensor to determine a fluid pressure within the medical device.

In another embodiment, the medical device has a pumping means that is powered by a rechargeable battery.

In another embodiment, the medical device has a pumping means that is powered by a rechargeable battery rechargeable through wireless energy transfer.

In another embodiment, the medical device has a dialysate chamber formed in arrays or a layered form.

In another embodiment, the medical device has a catheter to convey fluid from inside a dialysis chamber to the urinary bladder of a patient.

In another embodiment, the fibrosis cage of the medical device is positioned in an abdominal area of the patient, and in front of the peritoneal membrane of the patient.

In another embodiment, the medical device has a fibrosis cage having a porous opening facing the peritoneal membrane of the patient.

In another embodiment, the medical device has an external dialysate cleansing unit containing a sorbent capable of removing waste components and ions from dialysate.

In another embodiment, the medical device has a pumping means selected from the group consisting of the pumping means is one selected from the group consisting of a bellows pump, a peristaltic pump, a pulsatile pump and a syringe pump.

In another embodiment, the medical device has a pumping means regulated to maintain a maximum pressure change of 25 mmHg between the inside volume of a fibrosis cage of the medical device and the peritoneal cavity of a patient.

In another embodiment, the medical device has a pumping means regulated to not exceed a maximum pressure change of 25 mmHg between the inside volume of a fibrosis cage of the medical device and the peritoneal cavity of a patient.

In another embodiment, the medical device has a pumping means regulated to not exceed a maximum pressure change of any selected from 5, 15, 20, 25, 30, 35, 40, 45 and 50 mmHg, wherein the pressure difference is a pressure difference between the inside volume of a fibrosis cage of the medical device and the peritoneal cavity of a patient.

In another embodiment, the medical device has an electrodialyzer that applies an electrical field to concentrate ions and waste components into a plurality of chambers using an electrical potential.

In another embodiment, the medical device has an electrodialyzer that is in fluid communication with the patient's urinary bladder.

In another embodiment, the medical device has a means for sensing fluid volume in a patient wherein the means for sensing fluid volume is electrical impedance plethysmography or an arterial pressure measurement.

In another embodiment, the medical device is used to remove bulk fluid or excess fluid from a patient.

In another embodiment, the medical device has a dialysis chamber and a pumping means that function to allow excess fluid from a patient to be removed from the patient and expelled through an outlet of the dialysis chamber.

In another embodiment, the medical device has a dialysis chamber containing a membrane, wherein the membrane contacts extracellular fluid or bodily fluids of a patient.

In another embodiment, the medical device has a dialysis chamber in fluid communication with a fibrosis cage, wherein the dialysis chamber is located outside of the fibrosis cage.

In another embodiment, the medical device has a dialysis chamber in fluid communication with a fibrosis cage, wherein the dialysis chamber is located outside of the body of a patient.

In another embodiment, the medical device has a dialysis chamber, wherein a fresh supply of the dialysate is supplied to the dialysis chamber.

In another embodiment, the medical device has a dialysis chamber, wherein a fresh supply of the dialysate is supplied to the dialysis chamber and a dialysate exiting an outlet of the dialysis chamber is not contacted with a sorbent or a dialysate cleansing unit.

In another embodiment, the medical device removes excess fluids from patients having cardio-renal syndrome. The device has a fibrosis cage, a pump within the cage, and a catheter leading to the bladder. The medical device can also have electronics such as a negative pressure sensor and a wireless charger. The medical device can be self-contained and remove a few liters of fluid a day from a patient.

In yet another embodiment, a method has the steps of introducing a dialysate into a patient in need thereof, and dialyzing bodily fluid or extracellular fluid intra-corporeally. Other embodiments include the steps of inducing a pressure difference across the peritoneum of a patient to increase the total volume of fluid in an implanted medical device, dialyzing bodily fluids or extracellular fluid across a membrane using dialysate inside the implanted medical device, and inducing a pressure difference across the peritoneum to decrease the total volume of fluid in the implanted medical device. Still other embodiments contemplate the step of cleansing the dialysate in a closed loop cleaning process.

In another embodiment, a medical device is applied to the use of treating a patient by performing a method of treatment, wherein the medical device has a partially porous mesh that forms a fibrosis cage upon implantation into the patient and the fibrosis cage defining a space for accessing fluid from the patient, and the method of treatment comprises inducing a pressure difference across the peritoneum of a patient to increase a total volume of peritoneal fluid in an implanted medical device and performing one or more steps selected from the group consisting of: 1) dialyzing the blood across the peritoneal membrane, wherein peritoneal fluid is conveyed to a space inside of the implanted medical device and then conveyed to a dialysis chamber having a dialysate to reduce the concentration of waste components in the peritoneal fluid conveyed to implanted medical device; 2) dialyzing the blood across the peritoneal membrane, wherein peritoneal fluid is conveyed to an inside of the implanted medical device and then contacted with a dialysis chamber having dialysate to reduce the concentration of waste components in the peritoneal fluid conveyed to the implanted medical device and using an electrical potential to regenerate the dialysate; and 3) removing excess fluid from the patient by removing at least part of the fluid from implanted medical device from the patient. The method of treating the patient further includes inducing a pressure difference across the peritoneum to decrease the total volume of fluid in the implanted medical device and return fluid from inside the medical device to the patient.

In another embodiment, a device is applied to a use for removing waste components or fluid, the device having a partially porous mesh and a fibrosis forming surface defining a space for accessing extracellular fluid and a pump for moving extracellular fluid into and out of the space, the use including reducing the concentration of waste components in extracellular fluid or removing extracellular fluid.

In another embodiment, an implantable medical device has a partially porous mesh and a fibrosis-forming surface forming a fibrosis cage that defines a space for accessing a fluid, wherein the device is capable of inducing a relative pressure difference inside the fibrosis cage and can perform any one of conveying a fluid to the space inside the implanted medical device and then conveying the fluid to a dialysis chamber having a dialysate to reduce the concentration of waste components in the fluid conveyed to the implanted medical device; conveying a fluid to the space inside the implanted medical device and then conveying the fluid to a dialysis chamber having a dialysate to reduce the concentration of waste components in the fluid conveyed to the implanted medical device and using an electrical potential to regenerate the dialysate; and removing excess fluid by removing at least part of the fluid from the implanted medical device, and also inducing a pressure difference to decrease the total volume of fluid in the implanted medical device.

In additional embodiments, dialysis is performed across the membrane using a pump. In yet another embodiment, the step of expelling an effluent dialysate extra-corporeally is contemplated. Still yet another embodiment has the step of dialyzing bodily fluids or extracellular fluid using an electrical potential and directing the effluent filtrate to the patient's bladder. Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

DETAILED DESCRIPTION OF THE INVENTION

Figure 1:
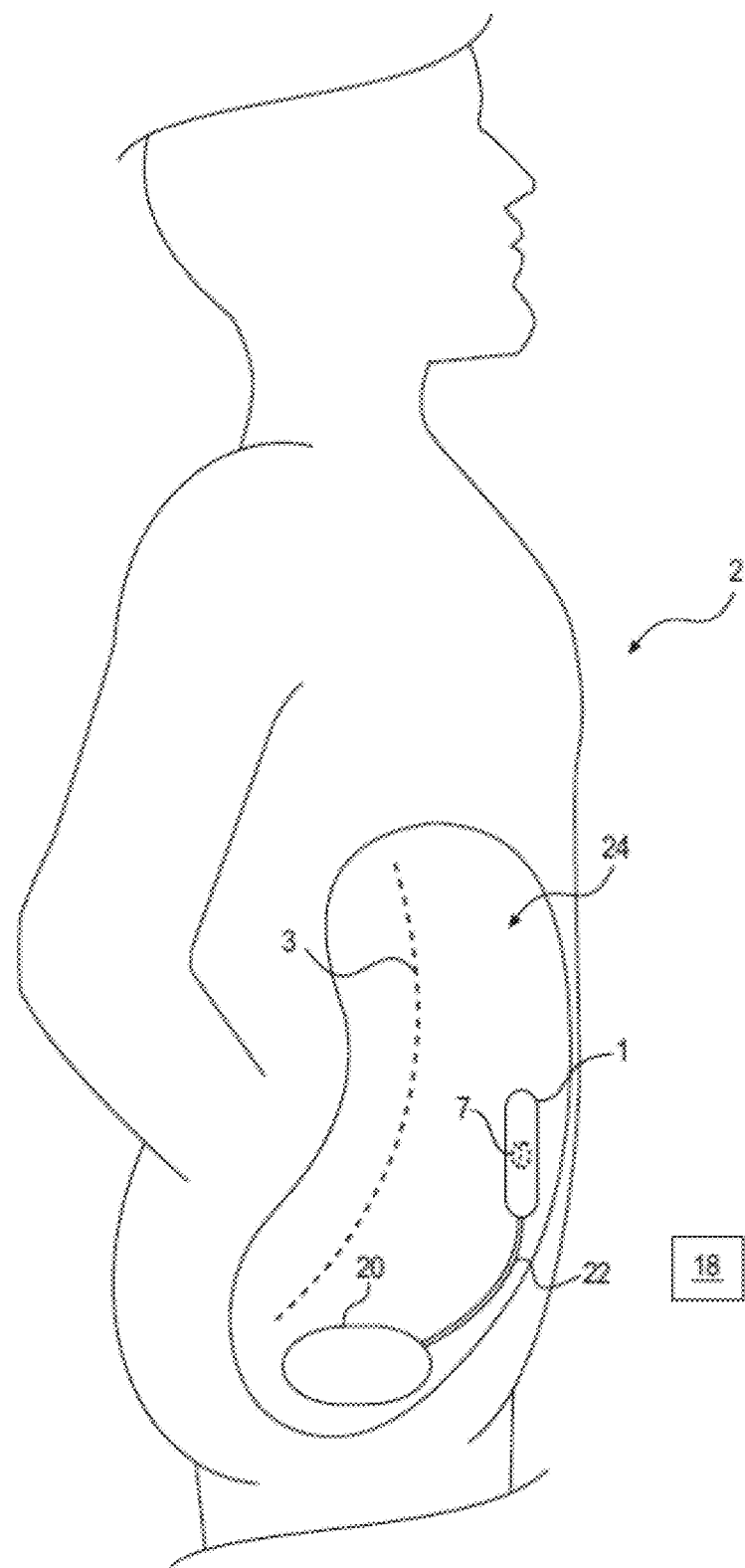
FIG. 1 is a diagram of a partially implantable embodiment of a medical system for removing fluid from the peritoneum of a patient and conveying the fluid to the urinary bladder.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "adjustable voltage generator" is an electrical component capable of delivering and maintaining varying magnitudes of voltage to other electronic components. The voltage delivered may be determined by a user, or a programmable control unit.

A "bellows pump" is a pump capable of creating an alternating positive and negative pressure within a confined space.

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail completely.

The terms "communicate" and "communication" include, but are not limited to, the connection of system electrical elements, either directly or remotely, for data transmission among and between said elements. The terms also include, but are not limited to, the connection of system fluid elements enabling fluid interface among and between said elements.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

A "control system" consists of combinations of components that act together to maintain a system to a desired set of performance specifications. The performance specifications can optionally include sensors and monitoring components, processors, memory and computer components configured to interoperate.

A "controller" or "control unit" is a device which monitors and affects the operational conditions of a given system. The operational conditions are typically referred to as output variables of the system, which can be affected by adjusting certain input variables.

The term "dialysate" describes a fluid into which solutes from a fluid to be dialyzed diffuse through a membrane.

"Dialysis" is a type of filtration, or a process of selective diffusion through a membrane. In certain embodiments, dialysis removes solutes of a specific range of molecular weights via diffusion through a membrane from a fluid to be dialyzed into a dialysate. In other embodiments, dialysis can remove an amount of bulk fluid volume from a subject or patient by passage of fluid through a membrane due to a pressure difference across the membrane; the pressure difference can be created by a pump in some embodiments. In certain embodiments, bulk fluid volume can be removed from the blood or extracellular fluid to affect fluid removal from the patient or subject. During dialysis, a fluid to be dialyzed is passed over a filter membrane, while dialysate is passed over the other side of that membrane. Dissolved solutes such as ions, urea, and other small molecules are transported across the filter membrane by diffusion between the fluids or a volume of fluid crosses from one side of the membrane to the other. The dialysate can be used to remove solutes and/or bulk fluid volume from the fluid to be dialyzed, and does not necessarily require the removal of waste via diffusive dialysis.

A "dialysis chamber" as used herein is a chamber in which dialysis is performed. A dialysis chamber contains or has a dialysis membrane for the performance of "dialysis" as defined above. The dialysis membrane can be provided in any useful configuration known to those of ordinary skill in the art including provided as an arrangement of several hollow fibers, tubes, microfibers or microtubes to maximize a ratio between surface area of the dialysis membrane and a volume of dialysate. The dialysis membrane can refer to a semipermeable barrier selective to allow diffusion of solutes of a specific range of molecular weights through the barrier, or optionally a high-permeability membrane, which is a type of semipermeable membrane that is more permeable to water than the semipermeable membrane of a conventional dialysis membranes having a semipermeable membrane that has a relatively low permeability to water. In certain non-limiting examples, the high-permeability semipermeable membrane has an in vitro filtration coefficient (Kuf) greater than 8 milliliters per hour per conventional millimeter of mercury, as measured with bovine or expired human blood while a conventional semipermeable membrane has a filtration coefficient (Kuf) less than 8 milliliters per hour per convention millimeter of mercury. One of ordinary skill in the art will understand that alternative and various configurations, materials and values in performance and fabrication of the dialysate chamber and/or membrane can be made and used without departing from the invention.

An "electrodialysis unit" as used herein is a fluid processing unit that removes waste components from effluent dialysate by altering the ionic composition of a fluid. Such units may include electrically conductive plates separated by ion-exchange membranes. Fluid flowing between the plates is exposed to an electrical field. The electrical field induces a rate of ion movement within the fluid corresponding to the magnitude of the voltage potential formed between the electrically conductive plates.

A "dialysate cleansing unit" as used herein is a fluid processing unit that removes waste components from effluent dialysate via sorbent adsorption.

The term "effluent dialysate," as used herein describes the discharge or outflow after the dialysate has been used for dialysis.

A "fibrosis cage(s)" as used herein describes a fibrogenic mesh encased in fibrotic tissue and having an empty internal cavity containing the components of the implantable medical device as well as bodily fluids.

The term "filtration" refers to a process of separating solutes from a fluid, by passing the fluid through a filter medium across which the solutes cannot pass.

The term "implantable," as used herein describes a device, component or module intended to be totally or partially introduced, surgically or medically into a mammalian body, or by medical intervention that remains after the procedure.

The term "hyperosmotic" pertains to a solution that has a higher solute concentration than another solution. In the human body, a hyperosmotic state refers to a condition caused by the accumulation in the body of significant quantities of osmotically active solutes.

The term "hypoosmotic" pertains to a solution containing a lower concentration of osmotically active components than a standard solution. In the human body, a hypoosmotic state describes a cell that has a lower concentration of solutes than its surroundings.

The term "intracorporeal," as used herein means existing within the body.

Osmolarity is defined as the number of osmoles of a solute per liter of solution. Thus, a "hyperosmolar solution" represents a solution with an increase in osmolarity compared to physiologic solutions. Certain compounds, such as mannitol, may have an effect on the osmotic properties of a solution as described herein.

The term "mesh" or "porous mesh" refers to a porous substructure that can be optionally wrapped in a material that blocks the passage of cells. The "mesh" or "porous mesh" creates or defines an acellular space or substantially acellular space within the body of the patient, where the "mesh" or "porous mesh" allows for the passage or diffusion of ions, urea and other small molecules, and water while substantially preventing the passage of cells. The "mesh" or "porous mesh" creates or defines an acellular space from which fluid can be removed from the patient or fluid from the peritoneum can be treated by dialysis or electrodialysis.

A "patient" is a member of any animal species, preferably a mammalian species, optionally a human. The subject can be an apparently healthy individual, an individual suffering from a disease, or an individual being treated for a disease.

A "pressure gauge" is a device that measures pressure, which is the force per unit area applied in a direction perpendicular to the surface of an object. Gauge pressure is the pressure relative to the local atmospheric or ambient pressure.

The term "programmable" as used herein refers to a device using computer hardware architecture and being capable of carrying out a set of commands, automatically.

The term "sensory unit" refers to an electronic component capable of measuring a property of interest.

The term "total volume of fluid" refers to the total volume of extracellular fluid and dialysate within the medical device or fibrosis cage. The total volume of fluid can be controlled, in some embodiments, through a pump or pump means that modifies the volume of space accessible to extracellular fluid and/or dialysate within the medical device or fibrosis cage. Specifically, in some embodiments, a pump or pump means can increase the volume of space to affect an influx of dialysate and/or extracellular fluid within the medical device or fibrosis cage and a pump or pump means can decrease the volume of space to affect an efflux of dialysate and/or extracellular fluid from the medical device.

The terms "treating" and "treatment" refer to the management and care of a patient having a pathology or condition. Treating includes administering one or more embodiments of the present invention to prevent or alleviate the symptoms or complications or to eliminate the disease, condition, or disorder. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a patient.

The term "waste components" as used herein describe waste organic and inorganic components, such as urea, uric acid, creatinine, chlorides, inorganic sulfate and phosphate. Specific "waste components" can vary between individual depending on diet and environmental factors. Hence, the term is intended to encompass any waste component that is normally removed by a kidney or by dialysis without restriction on the specific type of waste.

A "wearable dialyzer" is a portable artificial kidney device through which blood is circulated as the user moves through his daily routine, the dialyzing fluid being regenerated by a system of filters and make-up solids continuously fed to the dialysis fluid. The device may be a continuously internally operable and externally regenerable dialysis device that is capable of concurrently dialyzing a confined dialysis fluid against body fluids within the body and regenerating the dialysis fluid outside the body.

Implantable Peritoneal Cage

The present invention can be used for the treatment of chronic kidney disease, either as a replacement for a failed organ, or to reduce the need for dialysis. Furthermore, it can be configured to work as a stand-alone system wherein ambulatory dialysis is carried out by the system, or as an auxiliary system for hospital dialysis systems.

The present invention can employ a fibrosis cage, a pumping means, and an optional dialysis chamber. Further, the present invention can optionally employ a sensory unit, a controller, and an electrodialysis unit.

Referring to FIG. 1, an embodiment of a system for removing fluid from the body of a patient is described. A fibrosis cage 1 is formed by implanting a partially porous fibrogenic mesh 1 into a patient's body 2. The mesh can be treated with a surface coating of fibrosis-inducing agents, or extracellular matrix components which promote the growth of fibrous tissue. The mesh can also be covered with a material that is impermeable to cells, such as a sheet of polyvinyl alcohol (PVA). The mesh can also be impregnated with a slow-release pharmacological agent which controls fibrous tissue growth. For example, pharmacological agents that promote or inhibit fibrous tissue growth can be used. The fibrosis cage is preferably located in the patient's abdominal area, in front of the peritoneal membrane 3. During a maturation period after implantation, the fibrogenic mesh 1 promotes the growth of a fibrous tissue (shown below) which encapsulates the mesh thereby forming the fibrosis cage. The fibrosis cage has a porous opening facing the peritoneal membrane 3 through which extracellular fluid enters the cage. The peritoneal membrane 3 is represented by a dashed line in FIG. 1 to illustrate the boundary between the peritoneal fluid and the blood of the patient. After the maturation period, a space inside the fibrosis cage is mostly void of cellular matter, and is full of extracellular fluid from the peritoneum. Such cellular matter includes red blood cells, white blood cells, polymorphonuclear neutrophils, macrophages, and lymphocytes.

As illustrated in FIG. 1, in order to expedite the diffusion of fluid in and out of the cage, a pump or pumping means 7 is provided. The pump or pumping means 7 is not limited to any particular type of pump or any particular location. In certain embodiments, the pump or pumping means 7 is located outside of the cage 1. In some embodiments, the non-limiting pump or pumping means 7 can be a bellows pump, a peristaltic pump, a syringe pump or a pulsatile pump. The pump or pumping means 7 forces fluid in and out of the cage periodically via expansion and contraction or another pumping mechanism. The pump or pumping means 7 can be driven by an implanted rechargeable battery, or an externally supplied magnetic field. In certain embodiments, the rechargeable battery is rechargeable by wireless energy transfer. An optional pressure gauge can be present to monitor the fluid pressure within the fibrosis cage. A controller 18 can be present to control the operation of the pump or pumping means 7. The controller 18 can in certain embodiments be located outside the body 2 of the patient and can communicate with the pump or pumping means 7 wirelessly.

In certain embodiments, the pump or pumping means 7 is located inside of the peritoneal cage. The pump or pumping means 7 can be provided in locations outside of the fibrosis cage. In some embodiments the pumping means 7 can be placed adjacent to the cage in a manner where the pump or pumping means 7 can modulate the pressure within the fibrosis cage. In other embodiments, the pump or pumping means 7 can be connected to the fibrosis cage through any suitable means. In still other embodiments, the pump or pumping means 7 can be connected to the cage with tubing. The pump or pumping means 7 can optionally be connected to a catheter entering into the urinary bladder.

In FIG. 1, fluid is removed from the patient by means of the pump or pumping means 7 drawing extracellular fluid from the peritoneum of the patient into the cage 1 and transporting at least part of the fluid drawn into the cage 1 to the urinary bladder 20 by means of a catheter 22 connecting the cage 1 and the urinary bladder 20. As such, fluid can be removed from the patient using an implantable system without the need for providing a supply of dialysate. In an alternate embodiment, the catheter 22 or another means can be used to remove fluid from the cage 1 extracorporeally without discharge to the bladder 20. That is, the catheter 22 or equivalent structure can pass out of the body through a port or incision such that fluid is discarded or collected outside of the body.

Figure 2:
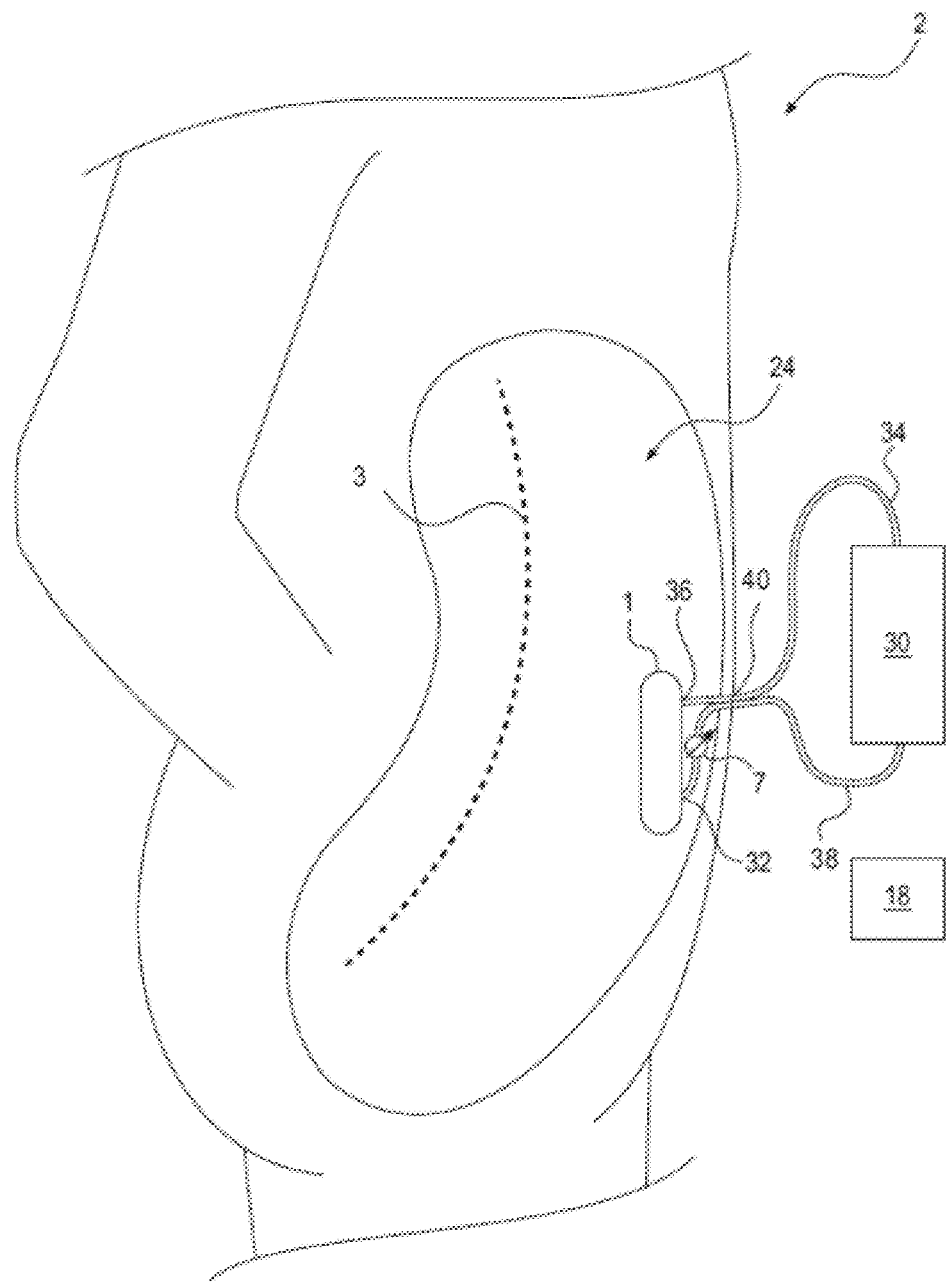
FIG. 2 is a partially implantable embodiment of a dialysis system having an external dialysis unit.

Referring to FIG. 2, a fibrosis cage 1 as in FIG. 1 is formed by implanting a partially porous fibrogenic mesh 1 into a patient's body 2. In FIG. 2, the system is provided to perform dialysis on the patient's blood via the peritoneal fluid. The system in FIG. 2 has a dialysis chamber with a membrane for performing dialysis, wherein fluid from the peritoneum via the implanted cage 1 is contacted with one side of the membrane and a dialysate is contacted with the other side of the membrane. Waste components diffuse across the membrane inside the dialysis chamber from the peritoneum to the dialysate. The fluid from the peritoneum having a reduced concentration of waste components is returned to the peritoneum cavity 24. Due to the removal of waste components from the peritoneal fluid, waste components diffuse from the blood of the patient across the peritoneum membrane 3. That is, the system shown in FIG. 2 removes waste components from the peritoneum fluid to maintain a concentration gradient in waste components between the patient's blood and the peritoneal fluid across the peritoneal membrane 3.

As shown in FIG. 2, a dialysis unit 30 is provided extracorporeally in fluid communication with the implanted cage 1. An outlet tube 34 is present connecting the dialysis unit 30 and an outlet 36 of the implanted cage 1. Similarly, an inlet tube 38 is present connecting the dialysis unit 30 and an inlet 32 of the implanted cage 1. Outlet tube 34 and inlet tube 38 enter the body through an incision or port 40 located on the body 2 of the patient. The dialysis chamber (not shown) can be present inside the dialysis cage 1 or the dialysis unit 30. In certain embodiments where the dialysis chamber is present in the implanted cage 1, the pump or pumping means 7 causes the influx and outflux of fluid from the peritoneum into the implanted cage 1 and the dialysis unit 30 provides a dialysate that is moved through the dialysis chamber inside the implanted cage 1. Due to the contact of the peritoneum fluid and the dialysate across the membrane in the dialysis chamber, waste components diffuse from the peritoneum of the patient to the dialysate. Further, a hydrostatic pressure difference across the membrane can cause the removal of fluid from the peritoneum and the patient. The dialysis unit 30 provides a source of dialysate including optionally a pump or other means to convey dialysate through the dialysis chamber. A supply of fresh dialysate can be provided wherein spent dialysate is discarded after passage through the dialysis chamber or a dialysate cleansing unit (described below) can be provided within the dialysis unit 30 to regenerate fresh dialysate from the dialysate exiting the cage 1 through outlet 36.

In other embodiments of the system shown in FIG. 2, the dialysis chamber is located within the dialysis unit 30. In such embodiments, peritoneal fluid is drawn into the implanted cage 1 through action of the pump or pumping means 7, which can be positioned intra- or extracorporeally. The peritoneal fluid is directed through outlet 36 and into outlet tube 34 to the dialysis unit 30 and dialysis chamber wherein the peritoneal fluid removed from the patient is dialyzed with a dialysate. The peritoneal fluid removed from the patient via the implanted cage 1 is then returned to the patient through the inlet tube 38 and inlet 32. Optionally, at least part of the peritoneal fluid removed from the patient can be discarded and not returned to the patient in order to cause a net removal of fluid from the patient. A supply of fresh dialysate can be provided wherein spent dialysate is discarded after passage through the dialysis chamber or a dialysate cleansing unit (described below) can be provided within the dialysis unit 30 to regenerate fresh dialysate from previously used dialysate. As described below, in any embodiment an electrodialysis unit can be provided to regenerate effluent dialysate from the dialysis chamber.

Figure 3:
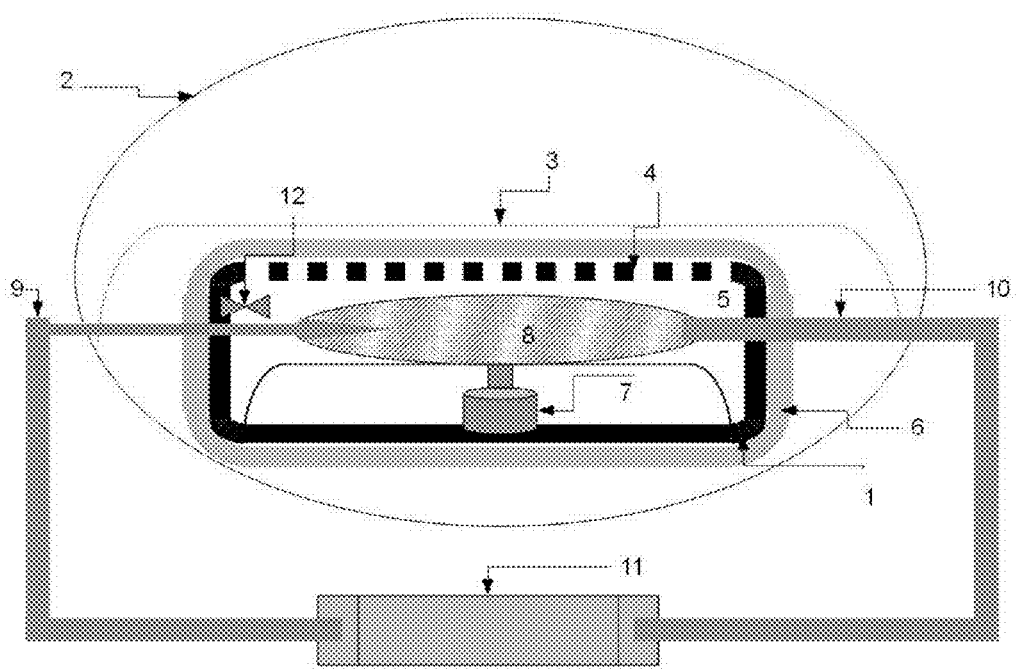
FIG. 3 is a block diagram of a partially implantable embodiment of the dialysis system having an external dialysate cleansing unit.

Referring to FIG. 3, an embodiment of a dialysis system according to the present invention having an optional external dialysate cleaning unit and a dialysis chamber within the implanted cage 1 is described. In some embodiments, a supply of fresh dialysate can be supplied in lieu of the optional external dialysate cleaning unit. A fibrosis cage is formed by implanting a partially porous fibrogenic mesh 1 into a patient's body 2. The mesh can be treated with a surface coating of fibrosis-inducing agents, or extracellular matrix components which promote the growth of fibrous tissue. The mesh can also be covered with a material that is impermeable to cells, such as a sheet of polyvinyl alcohol (PVA). The mesh can also be impregnated with a slow-release pharmacological agent that controls fibrous tissue growth. For example, pharmacological agents that promote or inhibit fibrous tissue growth can be used. The fibrosis cage is preferably located in the patient's abdominal area, in front of the peritoneal membrane 3. During a maturation period after implantation, the fibrogenic mesh 1 promotes the growth of a fibrous tissue 6 which encapsulates the mesh thereby forming the fibrosis cage. The fibrosis cage has a porous opening 4 facing the peritoneal membrane 3 through which extracellular fluid enters the cage. After the maturation period, a space 5 inside the fibrosis cage is mostly void of cellular matter, and is full of extracellular fluid. Such cellular matter includes red blood cells, white blood cells, polymorphonuclear neutrophils, macrophages, and lymphocytes. An alternative location to the abdominal area for the cage is inside the peritoneal cavity, which itself has low number of cells, thus rendering space 5 of the cage with even less cellular matter therein.

In certain embodiments, the fibrosis cage can be formed by two layers of materials. The first layer of material can be a metal or a plastic configured into a substructure that provides structural integrity to the overall device. The substructure is formed into any configuration such that passage of fluid through the substructure is unimpeded while the structural integrity of the substructure is maintained. In certain non-limiting embodiments, the substructure is formed into a mesh, a honey-comb, or any arrangement of evenly or unevenly spaced openings between which fluids can flow. Additionally, the first layer of material can be formed into a cage that prevents the collapse of the device under the pressure from the organs of the body. The substructure also allows the device to be able to sustain a negative pressure in the inner cavity of the device. The second layer of material is optional and can be a coating used to cover the fibrosis cage. Since the coating may not have a requisite structural strength, the coating can rely on the substructure to remain in place over the substructure. Due to the contact of the coating with tissue, the biocompatibility of the coating material is important. In particular, the coating material should not cause very thick fibrosis, should allow for the passage of fluids and ions, and should remain impermeable to the passage of cells. Many suitable materials known to those of ordinary skill can be used for the coating such as dialysis bags and woven polyesters. One particularly preferred material is poly vinyl alcohol (PVA) foam. A suitable, non-limiting thickness for a coating constructed from a PVA foam can be from about 1 mm to about 10 mm.

To demonstrate the feasibility of accessing bodily fluids using a fibrosis cage, a rodent model was implanted with stainless steel or polyester cages. Stainless steel cages were built in the shape of cylinders with a diameter of 1 cm and the ends of the cylinders were capped with Polydimethylsiloxane (PDMS). Afterwards, the stainless steel cages were wrapped in a sheet of polyvinyl alcohol (PVA) and the cages were sterilized using alcohol. The resulting devices were implanted subcutaneously in the backs of rats, two for each rat, for periods of one to five weeks. At the end of the study, animals were sacrificed and the devices were removed. Gross pathological examination of the explanted devices showed that there was about 1 mm thick fibrotic capsule formation around the device. Further examination indicated that the inside of the cage was cell and tissue free. As further described below, in vitro studies done using the explanted cages surrounded by fibrotic tissues showed that water, urea, sodium chloride and potassium chloride were all capable of diffusion through the fibrotic capsules and the cage walls.

As such, the fibrosis cage can be applied to a use of removing waste components, including urea and ions, from a fluid including extracellular fluid. Once waste components and/or fluid are present in an inside space of the fibrosis cage, the waste components can be removed by contact with a dialysis chamber, which can be located inside the fibrosis cage, or by the fluid containing the waste components being conveyed to a dialysis chamber at another location. The fibrosis cage can be further applied to the use of returning fluid without waste components or with a lowered concentration of waste components. As such, the fibrosis cage can be applied to the use of dialysis of the blood by lowering the concentration of waste components in the peritoneum. Alternatively, the fibrosis cage can be applied to the use of removing fluid from the peritoneum. Still further, the fibrosis cage can be applied to the use of removing fluid from the peritoneum and thereby removing fluid from the blood and other body compartments.

During the maturation period, a fibrous tissue 6 builds over the cage within a few weeks, leaving the inner space 5 acellular. As illustrated in FIG. 3, in order to expedite the diffusion of fluid in and out of the cage 1, a pump or pumping means 7 is placed therein or at another location. The pump or pumping means 7 is not limited to any particular type of pump. In some embodiments, the non-limiting pump or pumping means 7 can be a bellows pump, a peristaltic pump, a syringe pump, an impeller pump, a pulsatile pump, or any other suitable pump known to those of ordinary skill. One non-limiting example of an impeller type pump has an impeller rotatably positioned inside a housing wherein the impeller generates a rotating torque to enable movement of fluid. The pump or pumping means 7 forces fluid in and out of the cage 1 periodically via expansion and contraction or via another pumping mechanism. As shown in FIG. 3, a diaphragm 45 can be provided as part of the pump or pumping means 7 to assist in moving fluid in and out of the cage 1. The pump or pumping means 7 can be driven by an implanted rechargeable battery, or an externally supplied magnetic field. In certain embodiments, the rechargeable battery is rechargeable by wireless energy transfer. An optional pressure gauge 12 can monitor the fluid pressure within the fibrosis cage 1.

In certain embodiments, a dialysis chamber 8 within the fibrosis cage 1 is placed in front of the pump or pumping means 7 and remains in constant contact with the extracellular fluid from the peritoneum that is flowing in and out of the cage. In certain embodiments, due to the reduction in the concentration of waste components in the extracellular fluid, a concentration gradient between the blood and extracellular fluid across the peritoneal membrane is maintained to drive the dialysis of waste components from the blood across the peritoneal membrane 3. In other embodiments, bulk movement of fluid volume from the blood to the extracellular fluid, which can then be removed by the medical device, occurs across the peritoneal membrane 3 to assist bulk removal of fluid from a subject or patient. The dialysis chamber 8 includes a dialysis membrane across which exchange between a dialysate solution and extracellular fluid within space 5 occurs. The dialysate from the dialysis chamber 8 can be regenerated using an optional dialysate cleansing unit. Alternatively, a fresh supply of dialysate can be supplied to the dialysis chamber 8 to maintain a concentration gradient between the dialysate and the extracellular fluid. That is, in certain embodiments dialysis across a dialysis membrane is performed by providing a fresh supply of a dialysate to the dialysis chamber 8 wherein the dialysate is not regenerated by treatment with a sorbent or a dialysate cleansing unit.

The system shown in FIG. 3 performs dialysis by circulating a dialysate solution through the dialysis chamber 8 via inlet port 9 and outlet port 10 of the dialysis chamber 8. During dialysis, waste components in the extracellular fluid from the peritoneum contained within the fibrosis cage are transported by diffusion across the dialysis membrane of the dialysis chamber 8 to the dialysate. Effluent dialysate exits the dialysis chamber 8 via outlet port 10 and enters an optional external dialysate cleansing unit 11. The optional external dialysate cleansing unit 11 contains sorbents which are used to remove waste components such as urea and ions from the dialysate. The structure of the external dialysate cleansing unit 11 and sorbents is not limited provided that waste components are removed from effluent dialysate. In some embodiments, sorbents similar to the REDY sorbent system can be used. Roberts M. The regenerative dialysis (REDY) sorbent system, *Nephrology* 4:275-278, (1998). The dialysate cleansing unit 11 can also be provided in the dialysis unit 30 described in FIG. 2. Waste components include urea, potassium ions and various nitrate ions. The sorbent packages are cartridges which can be replaced by the patient when saturated by waste components. Once cleansed, the dialysate exits the external dialysate cleansing unit 11 and returns to the dialysate chamber 8 to continue dialysis. In an alternate embodiment, a supply of fresh dialysate is supplied to the dialysis chamber 8 and a dialysate cleansing unit is not present. That is, the dialysate exiting outlet 10 is discarded and replenished with fresh dialysate solution.

Figure 5:
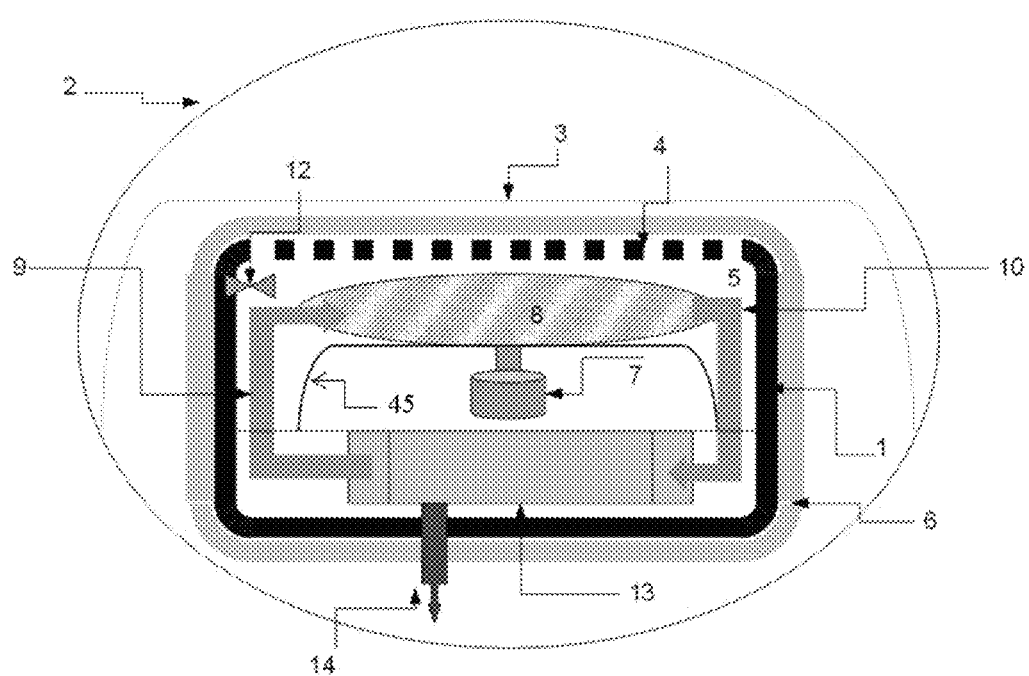
FIG. 5 is a block diagram of a fully implantable embodiment of the dialysis system having an internal electrodialysis unit.

Referring now to FIG. 5, another embodiment of a dialysis system according to the present invention having an electrodialysis unit is described. The embodiment of FIG. 5 is similar to that of FIG. 3, except the embodiment of FIG. 5 does not include an external sorbent-based dialysate cleansing unit, and instead includes an electrodialysis cleansing unit 13. FIG. 5 shows an electrodialysis cleansing unit 13 located internal to the fibrosis cage 1. In other embodiments, an electrodialysis cleansing unit 13 can also be provided in the embodiment described in FIG. 2 either inside the cage 1 or inside the dialysis unit 30. The embodiment of FIG. 5 also includes an optional catheter 14 for discharge of waste components to a patient's bladder or removed from the patient's body and either discarded or optionally treated In the embodiment of FIG. 5, dialysate cleansing is accomplished by electrodialysis. The electrodialysis unit 13 generates a pseudo urine and discharges it into the bladder via a catheter 14 or removed from the patient's body and either discarded or optionally treated. The electrodialysis unit 13 operates by applying direct current ("DC") electrical fields to the dialysate in order to change the osmolarity of the solution. The electrodialysis unit includes an adjustable voltage generator to generate electrical fields of varying magnitudes for selective removal of waste components.

In alternate embodiments, the electrodialysis cleansing unit 13 is located outside of the fibrosis cage and can be located outside of the body of the patient, such as in the dialysis unit 30 as shown in FIG. 2. In such embodiments, dialysate from the outlet port 10 of the dialysis chamber 8 is transported to an external electrodialysis unit (not shown) where the dialysate is treated. The dialysate can then either be treated by electrodialysis or the dialysate can be partially discarded with the remainder of the dialysate treated by electrodialysis. Then, the treated dialysate is retuned via the inlet port 9 of the dialysis chamber 8. The transport of dialysate from the dialysis chamber 8 to the electrodialysis unit can be accomplished by the pump or pumping means 7 or by an additional pumping means.

Figure 6:
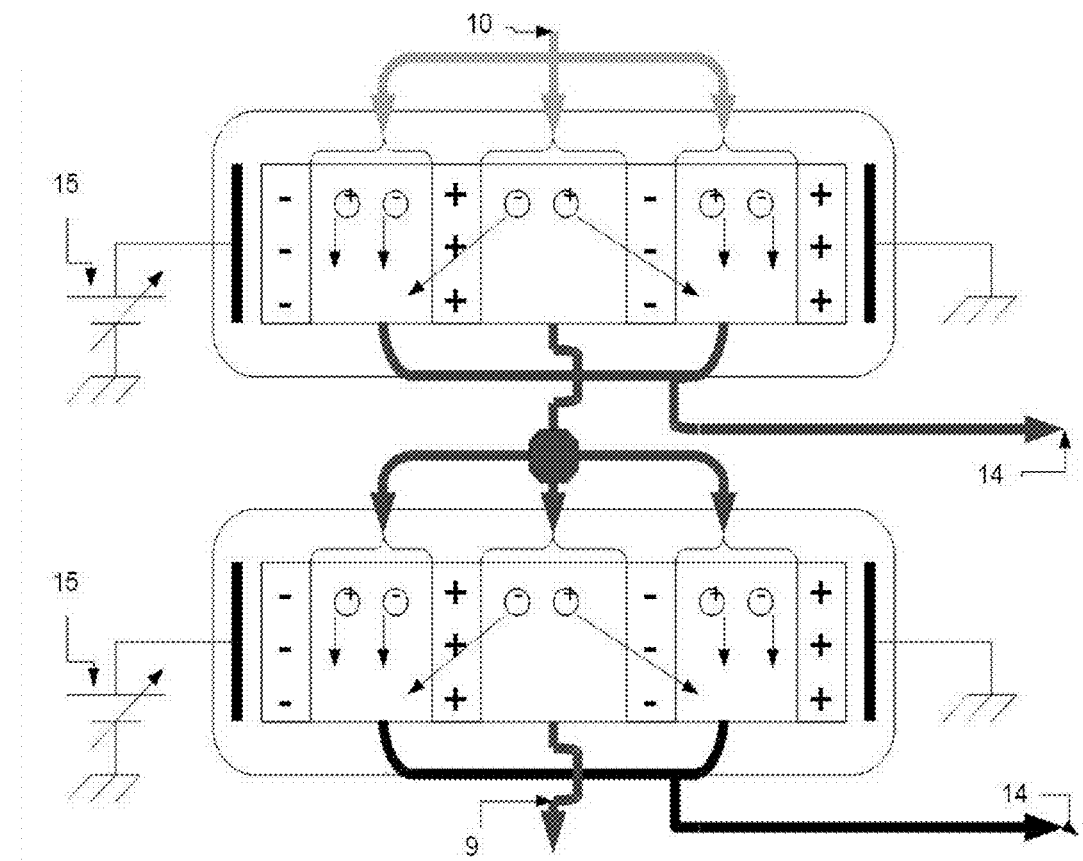
FIG. 6 shows the electrodialysis unit of FIG. 5 in greater detail.

Referring to FIG. 6, the electrodialysis unit 13 of FIG. 5 is shown in greater detail. Effluent dialysate enters the electrodialysis chamber via inlet port 10. Electrical fields generated by a power source 15 create an electric potential which drives movement of the ions to concentrate them in different chambers. Hypoosmotic dialysate exits the electrodialysis unit via outlet port 9 while a hyperosmotic dialysate solution is discharged into the urinary bladder or removed from the patient's body and either discarded or optionally treated via outlet port or catheter 14. The hypoosmotic dialysate returns to the dialysate chamber 8 of FIG. 5 to continue dialysis.

By adjusting the electric potential generated by the power source 15, the osmolarity of the solutions can be controlled, permitting regulation of fluid and salt removal from the dialysate, and in turn from the patient. The device can be built as a completely implantable system, and can be powered by an internal or external power source, or a combination of an internal and external power source. Power sources may include implanted batteries or an external magnetic field. A programmable controller can regulate fluid and salt extraction and flow rates through the system.

In both of the embodiments shown by FIGS. 3 and 5, the growth of fibrotic tissue over the dialysis chamber 8 is prevented because the dialysis chamber is located inside the fibrosis cage. This in turn prolongs the useful life of the dialysis chamber 8 and provides a safe environment for dialysis to take place. Furthermore, by physically isolating the dialysate from the body, the risk of infection is reduced dramatically. In the event that a pathogen was to enter the dialysis chamber 8, the pathogen would not be able to pass through the dialysis membrane and infect the patient.

In an additional embodiment, the implanted cage and the pump within are used to extract fluid from the body and to direct the extracted fluid to the urinary bladder to treat fluid overload in a patient with heart failure or cardio-renal symptoms, as shown in FIG. 1. This embodiment can be totally implantable within the patient, where a drainage catheter connects the fibrosis cage to the urinary bladder for conveyance of extracted fluid to the urinary bladder. Optionally, the conveyance of the extracted fluid from the fibrosis cage to the urinary bladder can be assisted and/or controlled with an additional pump. To reduce the calcification of the drain catheter, piezoelectric vibrators can be placed around the catheter and periodically excited. Piezoelectric vibrators can also be provided in association with catheter 14 and 22 as shown in FIG. 1 or 5. Operation of the device in this embodiment can be open loop to extract a certain amount of fluid each day, governed by the patient based on a personal feedback mechanism such as body weight, or controlled by an electronic unit and its optional feedback sensor such as electrical impedance monitor indicating the body fluid level.

Figure 7:
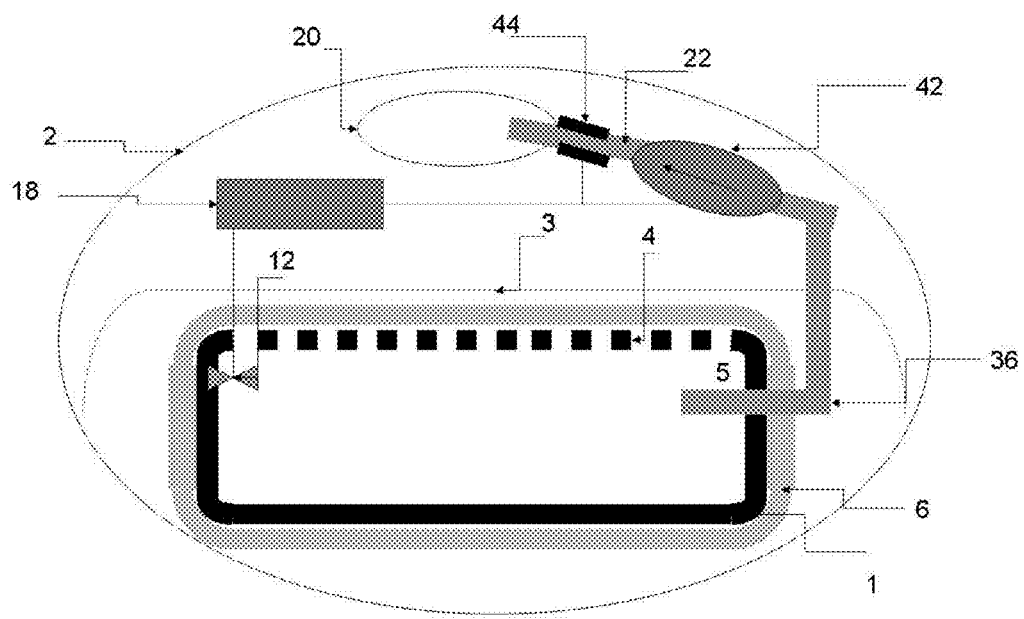
FIG. 7 shows an implantable embodiment of a medical system for removing fluid from the peritoneum of a patient and conveying the fluid to the urinary bladder.
Figure 8:
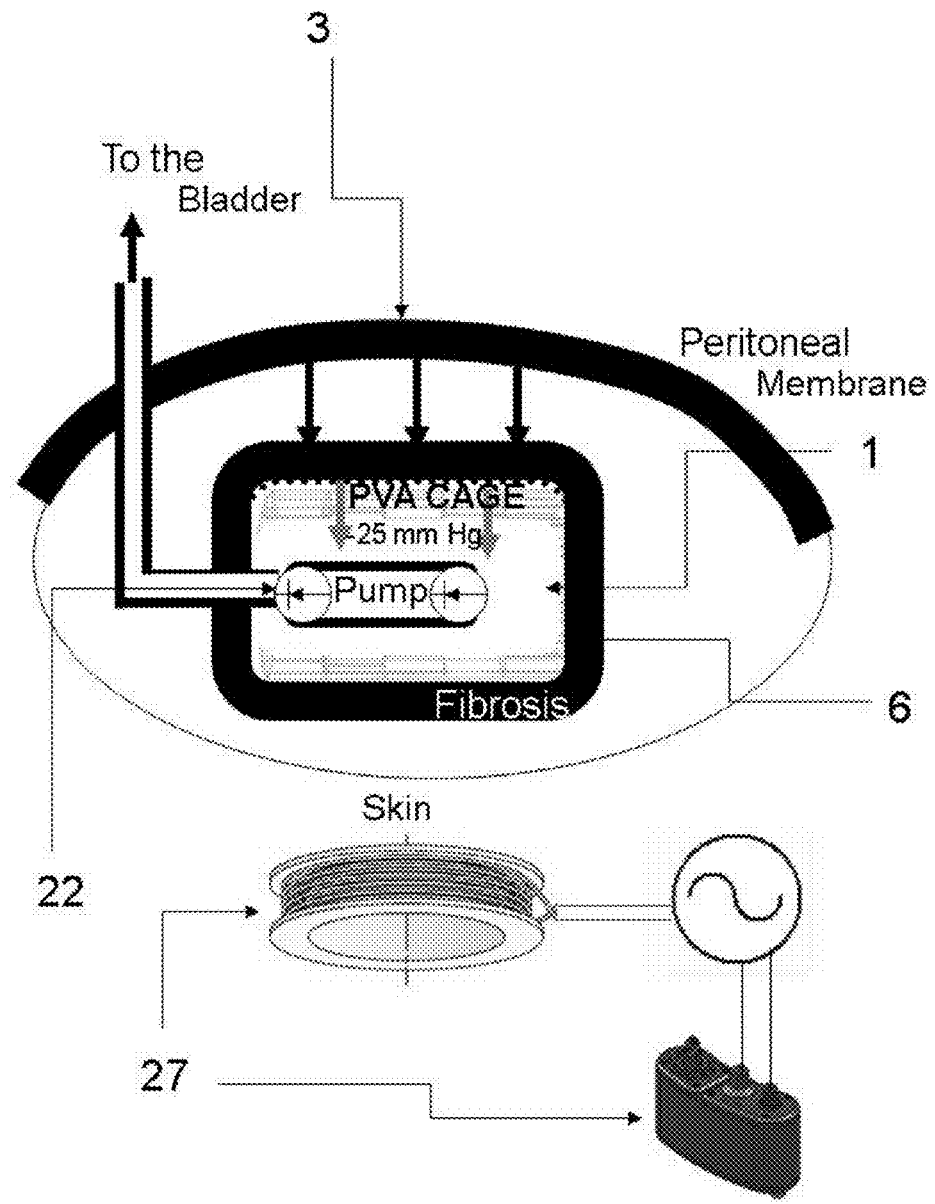
FIG. 8 shows the implantable embodiment of FIG. 7 with a wireless power supply unit for providing power to the medical system.

An alternate embodiment is shown in FIG. 7, which depicts a completely implantable implementation of the system. The fibrosis cage 1 with fibrotic capsule 6 is used to accumulate fluid within the device cavity 5 and fluid from the device cavity 5 is removed via the outlet 36. Pump 42, shown as external to the fibrosis cage 1, is used both for the generation of the negative pressure inside the device cavity 5 and also to pump the fluid via the outlet 36. Fluid is finally disposed into the urinary bladder 20 via the catheter 22. The pumping action commences only when the controller 18 determines that the pressure inside the device cavity 5 is equal of more than −25 mm Hg. Pressure sensing is done by the pressure gauge 12. Additionally, the piezoelectric vibrators 44 are activated by the controller 18 to reduce calcification on the inner walls of the catheter 23. In this embodiment, all components are implanted and power can be supplied via an external unit 47 shown in FIG. 8. Implementation depicted in FIG. 8 shows an embodiment where the pump 42 is located internal to the fibrosis cage where other elements are as described in FIG. 7.

In alternate embodiments of the system shown in FIG. 7, the catheter 22 or another means can be used to remove fluid from the cage 1 extracorporeally. That is, the catheter 22 or equivalent structure can pass out of the body through a port or incision such that fluid is discarded or collected outside of the body.

Embodiments of the dialysis system preferably include an electronic controller. The electronic controller can be used to maintain pressure within the system by regulating the total volume of fluid within the fibrosis cage. Additionally, the controller can adjust the dialysis rate of the system. The electronic controller may include a programmable control unit. A control feedback system may be formed by electrical or wireless data links between a control unit, pump or pump means 7 and the pressure gauge 12. A programmable control unit 18 is shown in FIGS. 1 and 2. Systems and methods for establishing communication between an external device and an implanted medical device have been developed, such as those described in U.S. Pat. No. 7,023,359, Goetz et al., the subject matter of which is incorporated herein by reference.

The control unit can also be able to detect a fluid overload situation within the system. In the event of fluid overload, the control unit reduces the volume of dialysate in the system in order to extract additional amounts of fluid from the patient. The electronic controller regulates the flow of dialysate through the dialysis chamber 8, and also monitors the amount of dialysate present in the dialysis chamber. A patient's fluid status can be measured using a variety of means, such as electrical impedance plethysmography and arterial pressure measurements.

The efficacy of dialysis performed by embodiments of the dialysis system is governed in part by the presence of cellular matter within the fibrosis cage. The presence of cellular matter within a dialysis system negatively influences diffusive mass transfer therein. Thus it is preferable to have a system which limits the presence of cellular matter in order to maintain the effectiveness of dialysis performed by the system.

The medical devices and methods described herein are not limited to the treatment of humans. Rather, the medical devices and methods described herein can be applied to other mammals including cats and dogs and other animals commonly kept as pets but also including exotic pets. Notably, cats oftentimes require dialysis as treatment for end-stage renal disease (ESRD). The terms "subject" and "patient" as used throughout this document include humans as well as other non-human mammals. Non-limiting examples of non-human mammals include monkeys, rabbits, gerbils, guinea pigs, hamsters, chinchillas, ferrets, mice, rats, pigs, horses, felines, canines, primates, hedgehogs, rodents, polecats, fennec foxes, tame silver foxes, red foxes, skunks, raccoons, capybaras, hedgehogs, arctic foxes, bears, coyotes, wolves and wolf/dog hybrids.

It is known that a pressure of (−)25 mmHg lower body negative pressure ("LBNP") is tolerated by humans. In certain embodiments, the pump or pumping means 7 is regulated not to exceed a maximum LBNP or pressure difference between the internal volume of the fibrosis cage of the medical device and the peritoneal cavity, for example, 25 mmHg. However, other non-limiting ranges for maximum pressure difference can include 10-50, 15-25, 17-29, 12-45, 23-28, and 21-38 mmHg. In some embodiments, the maximum pressure difference can be any one of 5, 15, 20, 25, 30, 35, 40, 45 and 50 mmHg. In further embodiments, the pump or pumping means 7 is regulated not to exceed a maximum LBNP or pressure difference within the medical device selected from any of 5, 10, 15, and 20 mmHg. The pumping means 7 can also be regulated to not exceed a maximum pressure difference of any one of 5, 15, 20, 25, 30, 35, 40, 45 and 50 mmHg. Furthermore, it is also known that the active peritoneal flow is approximately 30 mL/hr/cm-H$_2$O or 40 mL/hr/mmHg. Therefore, flow rate through the peritoneal membrane can be calculated as:

Flow=25 mmHg×40 mL hr$^{-1}$ mmHg$^{-1}$=1 L/hr

Since the flow must be reversed periodically to empty the chamber, the actual flow rate would be half of 1 L/hr, or 0.5 L/hr, yielding a maximum daily flow rate of 12 L/day.

Figure 4:
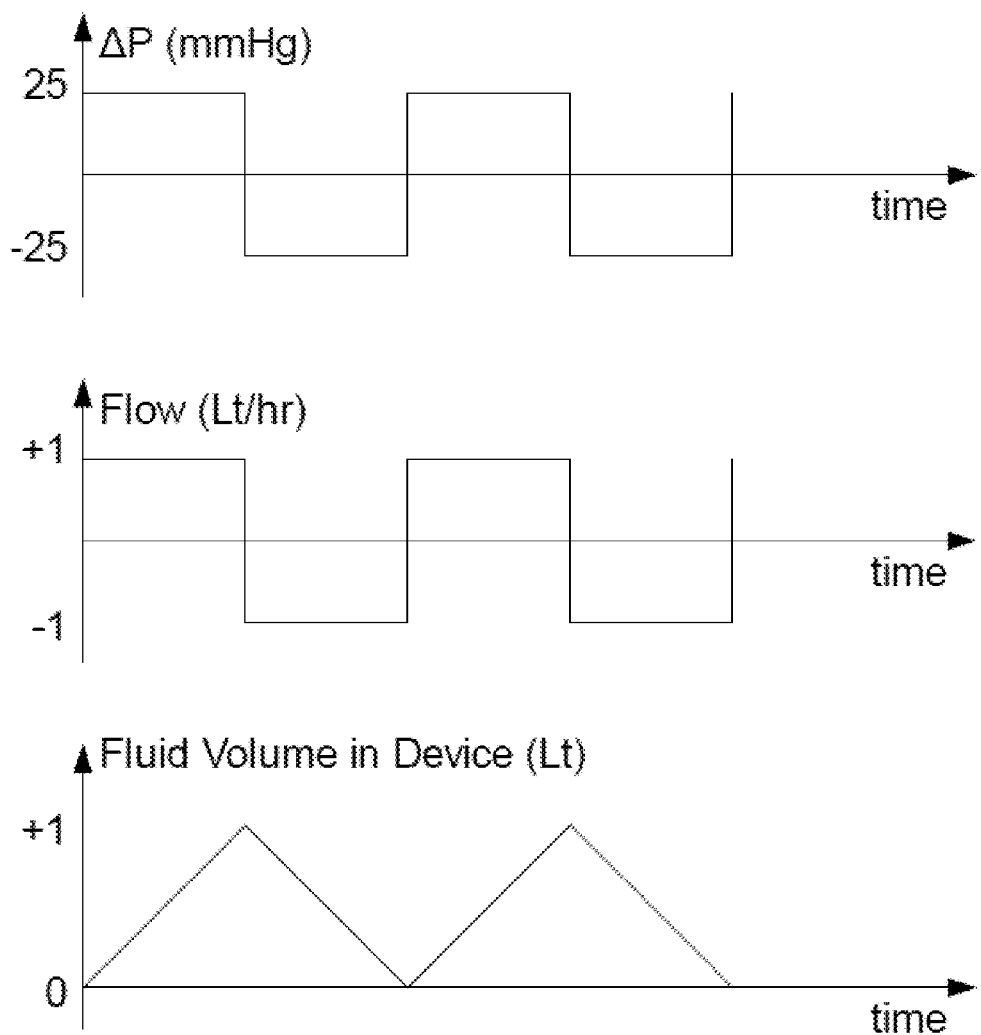
FIG. 4 is a graphical illustration of the pressure, flow, and volume relationship that exists during operation of the dialysis system.

In order to limit the pressure generated by the pump or pumping means 7, a pressure gauge 12 is utilized. During the generation of the positive and negative pressures that are necessary for the pumping action, the relative pressure change is measured and pumping is paused when the absolute value of the pressure change exceeds 25 mmHg. FIG. 4 shows a graphical representation of the pressure changes inside the fibrosis cage, fluid flow in and out of the cage, and fluid volume within the cage. As discussed above, a control unit in electrical or wireless communication with the pump or pumping means 7 and pressure gauge 12 may be used to regulate the pressure of fluid within the fibrosis cage.

It will be apparent to one skilled in the art that variations of the present invention are possible. For example, the dialysis chamber 8 can be constructed in layers, and additional layers can be used to increase the efficacy of dialysis. Modifications to the shape of the cage and the internal structures such as the pump or pumping means 7 can also be incorporated to improve the system dialysis function, anatomical fit, and cosmetic appearance of the device.

It will also be apparent to one skilled in the art that various combinations and/or modifications and variations can be made in the dialysis system depending upon the specific needs for operation. Moreover, features illustrated or described as being part of one embodiment may be used on another embodiment to yield a still further embodiment.

EXAMPLE

Figure 9:
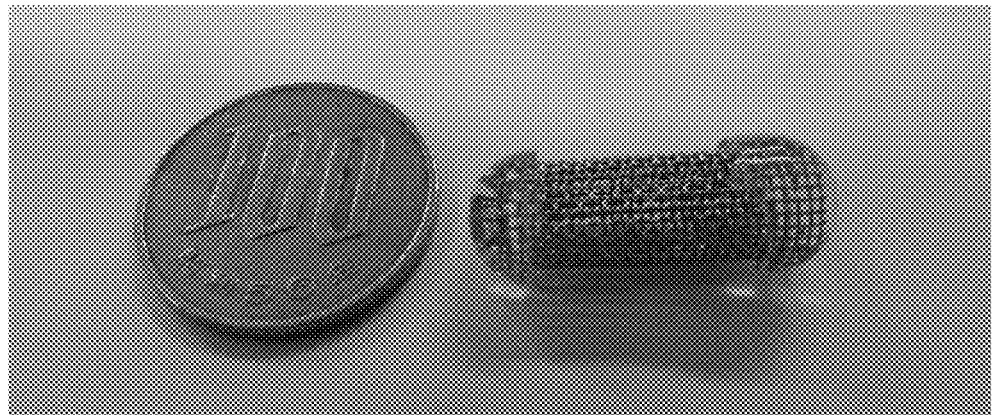
FIG. 9 shows an exemplary cage formed from stainless steel with poly(N,N-dimethylacrylamide) (PDMA) end caps and size shown relative to a Japanese 100 yen coin.

Cylinder shaped cages were formed using stainless steel and polyester meshes. Ends of the cylinders were capped using poly (N,N-dimethylacrylamide), also known as PDMA. A picture of the stainless steel cage can be seen in FIG. 9. The size the cage in FIG. 9 is shown relative to a Japanese 100 yen coin. Some of the cages were wrapped in poly vinyl alcohol (PVA) sheets. All cages were sterilized by dipping them in alcohol prior to implantation.

Figure 10:
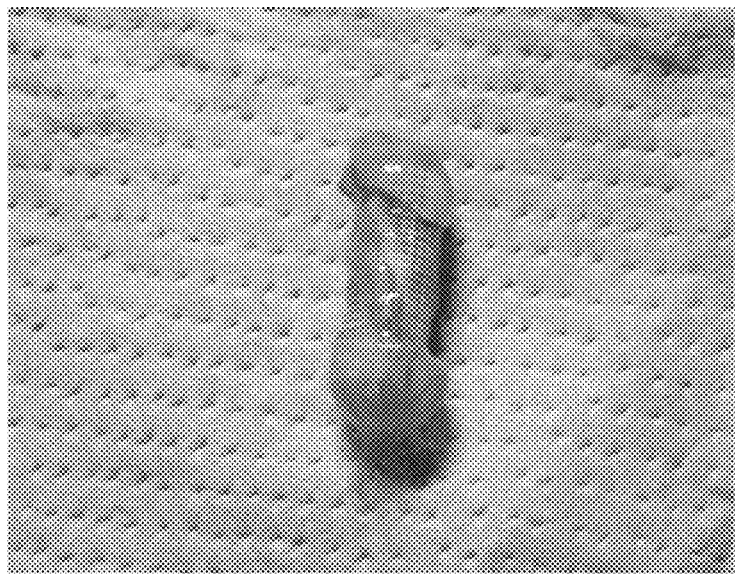
FIG. 10 shows an exemplary cage formed from polyester with a fibrotic capsule after implantation for a period of two weeks.
Figure 11:
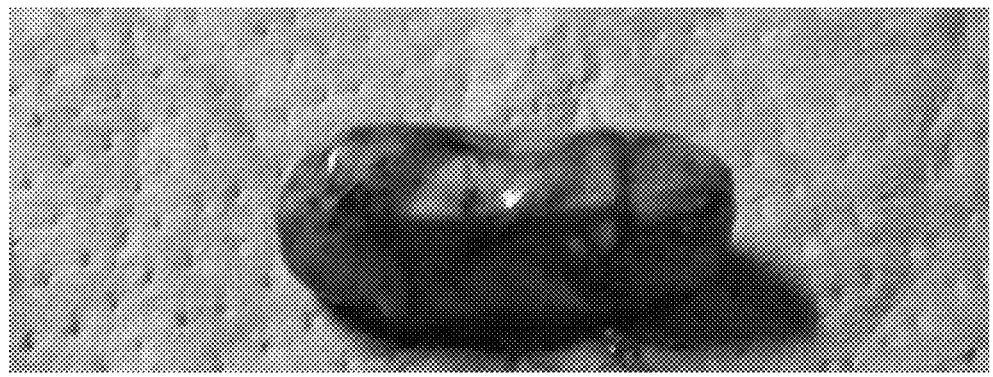
FIG. 11 shows an exemplary cage formed from steel wrapped in polyvinyl alcohol (PVA) with a fibrotic capsule after implantation for a period of two weeks.

Cages were subcutaneously implanted into rats on the back of the animals. Animals were anesthetized with ethyl ether and small incisions were made to place two cages in the back of each animal. Two weeks after the implantation of the cages, the animals were sacrificed and the cages were removed. As shown in FIGS. 10 and 11, the cages developed fibrotic capsules during the two weeks of implantation. FIG. 10 shows an exemplary cage formed from a polyester mesh having a fibrotic cage. FIG. 11 shows an exemplary cage formed from stainless steel wrapped in PVA prior to implantation having a fibrotic cage.

Procedures were carried out in vitro to measure the diffusion properties of the explanted device with its associated fibrotic capsule. First, one of the PDMA caps was removed to verify that the cages were free of tissue growth within the cage. After verification of the absence of internal tissue growth, the cages were partially inserted into hyperosmotic solutions to measure the changes in the concentrations of solutes within the cavity of the cages. Care was taken to keep the open end of the cage (having the PDMA cap removed) above the level of the hyperosmotic solution to prevent the solution from entering the cage by a route other than by diffusion across the fibrotic capsule.

Figure 12:
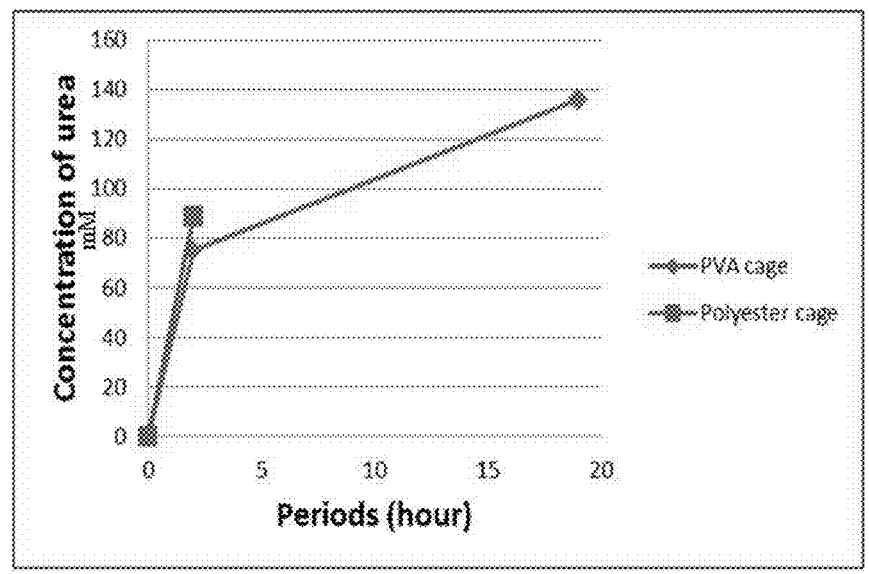
FIG. 12 shows a plot of the diffusion of urea across a polyester cage with a fibrotic capsule and across a stainless steel cage with a fibrotic capsule.

Two measurements were carried out to measure the diffusion properties of the fibrotic capsule. In the first study, the cage and the surrounding fibrotic capsule were partially immersed into a hyperosmotic urea solution. Periodically, fluid samples were taken from the inside of the cage to measure the urea concentration inside the cage. The results from this study are shown in FIG. 12, where the internal urea concentration (mM) increases as a function of time, which indicates that urea diffuses across the fibrotic capsule and the cage. Data for both a polyester cage and a stainless steel cage with PVA (PVA cage) are shown in FIG. 12.

Figure 13:
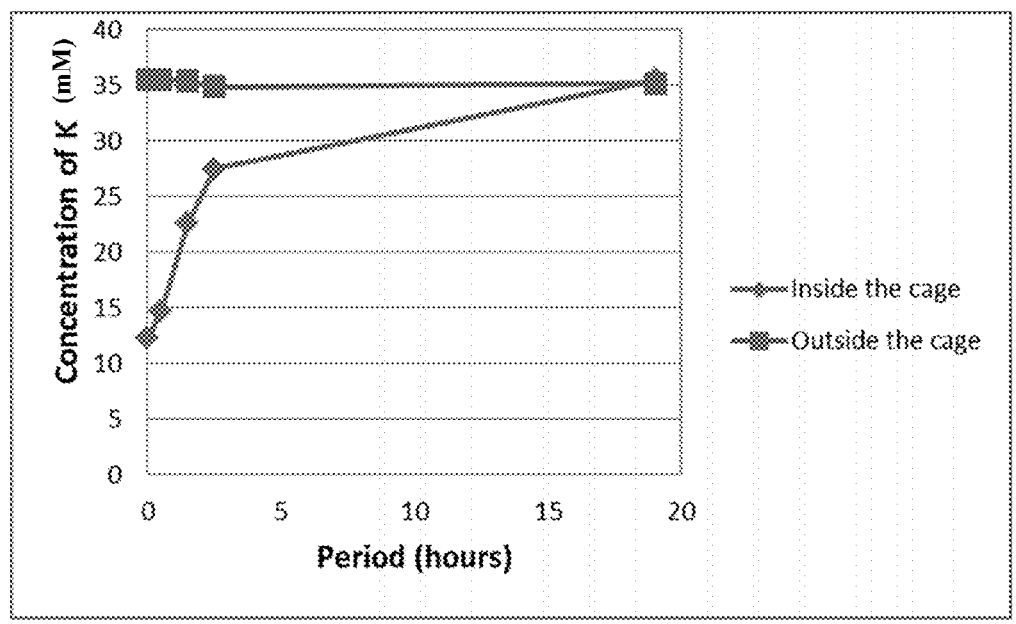
FIG. 13 shows a plot of the diffusion of potassium ions across a stainless steel cage wrapped in polyvinyl alcohol (PVA) with a fibrotic capsule.

In the second study, the diffusion of potassium ions was measured (mM) using a hyperosmotic potassium solution for a stainless steel cage with PVA and a surrounding fibrotic capsule. The procedure was the same as in the first study except a potassium chloride solution was provided. As shown in FIG. 13, potassium ions also diffuse across the fibrotic capsule and the cage.

Table 1 below shows the expected number of red blood cells ("RBC") and white blood cells ("WBC") in a patient's blood and peritoneal cavity. The values in Table 1 reflect typical ranges found in healthy individuals. As shown in Table 1, the cellular concentration is substantially reduced in the peritoneal cavity compared with the blood for all individuals regardless of physiological or disease state. As such, placement of the device in the peritoneal space or at a location having access to the peritoneal space reduces exposure to blood cells. Table 2 shows an exemplary reduction in counts of white blood cells, polymorphonuclear neutrophils ("PMN"), macrophages ("MP"), and lymphocytes ("LYMP") in a cage over the course of three weeks following implantation of the cage. Marchant et al., *In vivo* Biocompatibility Studies I: The Cage Implant System and a Biodegradable Hydrogel, J. Biomed. Mat. Res. 17:301-25 (1983).

TABLE 1

Expected cell counts in the blood and peritoneal cavity

| | RBC | WBC |
|---|---|---|
| Blood | 4.2-6.9 million/µL | 4,300-10,800/µL |
| Peritoneum | <10,000/µL | <500/µL |

TABLE 2

Cell count (cells/µL) interior to an implanted cage with time

| Day | Total WBC | PMN | MP | LYMP |
|---|---|---|---|---|
| 1 | 21600 | 20100 | 220 | 1300 |
| 3 | 11000 | 10100 | 170 | 770 |
| 4 | 4160 | 3500 | 110 | 570 |
| 5 | 2890 | 2080 | 84 | 720 |
| 7 | 820 | 390 | 43 | 390 |
| 8 | 730 | 180 | 60 | 490 |
| 11 | 450 | 42 | 70 | 340 |
| 14 | 260 | 12 | 14 | 230 |
| 17 | 250 | 4 | 11 | 240 |
| 21 | 120 | 2 | 14 | 100 |

We claim:

1. A medical device, comprising:
a partially porous mesh that forms a fibrosis cage upon implantation into a patient, the fibrosis cage defining a space for accessing fluid from the patient; a pumping means for pumping fluid into and out of the fibrosis cage; and a dialysis chamber for dialyzing the fluid from the patient having an inlet and an outlet for the movement of a dialysate through the dialysis chamber; wherein the dialysis chamber may be located either extracorporeally with respect to the patient or intracorporeally with respect to the patient.

2. The medical device of claim 1, wherein one side of the partially porous mesh has a porous opening.

3. The medical device of claim 1, further comprising a material impermeable to cells surrounding the partially porous mesh.

4. The medical device of claim 1, wherein the pumping means is one selected from the group consisting of a bellows pump, a peristaltic pump, a pulsatile pump, an impeller pump, and a syringe pump, said pumping means positioned inside the partially porous mesh, outside the partially porous mesh or adjacent to the partially porous mesh.

5. The medical device of claim 1, wherein the pumping means is regulated to not exceed a maximum pressure difference of any one of 5, 15, 20, 25, 30, 35, 40, 45 and 50 mmHg, wherein the pressure difference is a pressure difference between the inside of the fibrosis cage and a peritoneal cage of a patient.

6. The medical device of claim 1, further comprising a catheter to convey fluid inside the dialysis chamber to the urinary bladder of a patient.

7. The medical device of claim 1, further comprising a controller for regulating the fluid volume of the patent and adjusting a clearance rate of the patient.

8. The medical device of claim 1, further comprising a means for sensing a fluid volume of the patient, wherein the means for sensing fluid volume is an electrical impedance plethysmography or an arterial pressure measurement.

9. The medical device of claim 1, further comprising one or more selected from the group consisting of an external dialysate cleansing unit containing a sorbent capable of removing waste components and ions from the dialysate or an electrodialyzer in fluid communication with the dialysis chamber for regenerating the dialysate.

10. The medical device of claim 1, further comprising a means for delivering a fresh dialysate to the dialysis chamber.

11. A medical device, comprising:
a partially porous mesh that forms a fibrosis cage upon implantation into a patient, and a pumping means for pumping fluid into and out of the fibrosis cage, wherein at least part of the fluid pumped into the fibrosis cage is removed from the patient, further comprising a catheter configured to discharge at least part of the fluid pumped into the fibrosis cage to the urinary bladder of the patient and wherein the medical device further comprises one or more piezoelectric vibrators to reduce or to remove calcification from the catheter.

12. The medical device of claim 11, wherein the pumping means is one selected from the group consisting of a bellows pump, a peristaltic pump, pulsatile pump and a syringe pump, said pumping means positioned inside the partially porous mesh, outside the partially porous mesh or adjacent to the partially porous mesh.

13. The medical device of claim 11, wherein the pumping means is regulated to not exceed a maximum pressure change of any one of 5, 15, 20, 25, 30, 35, 40, 45 and 50 mmHg, wherein the pressure difference is a pressure difference between the inside of the fibrosis cage and a peritonea cavity of the patient.

14. The medical system of claim 11, wherein the medical device is powered by any selected from the group consisting of an internal battery, an externally coupled power source and a rechargeable battery wherein the rechargeable battery is rechargeable by wireless energy transfer.

* * * * *

UNITED STATES PATENT AND TRADEMARK OFFICE
CERTIFICATE OF CORRECTION

PATENT NO.       : 8,641,659 B2                                  Page 1 of 1
APPLICATION NO.  : 13/399910
DATED            : February 4, 2014
INVENTOR(S)      : Soykan et al.

It is certified that error appears in the above-identified patent and that said Letters Patent is hereby corrected as shown below:

In the Claims

Col. 20, Patent Line 53, Claim 5:
Delete: "... peritoneal cage of a patient." and insert: "... peritoneal cavity of a patient."

Col. 20, Patent Line 59, Claim 7:
Delete: "... fluid volume of the patent and ..." and insert: "... fluid volume of the patient and ..."

Col. 22, Patent Line 10, Claim 13:
Delete: "... cage and a peritonea cavity..." and insert: "... cage and a peritoneal cavity ..."

Signed and Sealed this
Fourteenth Day of October, 2014

Michelle K. Lee
*Deputy Director of the United States Patent and Trademark Office*